(12) United States Patent
Rava

(10) Patent No.: US 9,919,100 B2
(45) Date of Patent: Mar. 20, 2018

(54) SAFETY NEEDLE DEVICE

(71) Applicant: LEXEL S.R.L., Buenos Aires (AR)

(72) Inventor: Nestor Rava, Buenos Aires (AR)

(73) Assignee: LEXEL S.R.L., Buenos Aires (AR)

( * ) Notice: Subject to any disclaimer, the term of this patent is extended or adjusted under 35 U.S.C. 154(b) by 117 days.

(21) Appl. No.: 14/645,476

(22) Filed: Mar. 12, 2015

(65) Prior Publication Data
US 2016/0263313 A1    Sep. 15, 2016

(51) Int. Cl.
| | | |
|---|---|---|
| A61M 5/162 | (2006.01) |
| A61M 25/06 | (2006.01) |
| A61M 39/02 | (2006.01) |
| A61M 5/158 | (2006.01) |
| A61M 5/32 | (2006.01) |

(52) U.S. Cl.
CPC .......... *A61M 5/1626* (2013.01); *A61M 5/321* (2013.01); *A61M 5/3271* (2013.01); *A61M 25/0606* (2013.01); *A61M 25/0612* (2013.01); *A61M 39/02* (2013.01); *A61M 5/3243* (2013.01); *A61M 2005/1581* (2013.01); *A61M 2005/1583* (2013.01); *A61M 2005/1585* (2013.01); *A61M 2005/3247* (2013.01)

(58) Field of Classification Search
CPC .. A61M 2005/1581; A61M 2005/1585; A61M 2005/583; A61M 39/02; A61M 39/0247; A61M 2039/0294; A61M 5/1583; A61M 5/3213; A61M 5/3243; A61M 5/3245; A61M 5/3271; A61M 5/3275; A61M 2005/3247; A61M 2005/3252; A61M 2005/3256; A61M 25/0606; A61M 25/0612; A61M 5/1626
See application file for complete search history.

(56) References Cited

U.S. PATENT DOCUMENTS

| | | | | |
|---|---|---|---|---|
| 6,261,259 | B1* | 7/2001 | Bell | A61M 5/158 |
| | | | | 604/500 |
| 8,728,029 | B2* | 5/2014 | Vaillancourt | A61M 5/3213 |
| | | | | 604/110 |
| 2003/0083624 | A1* | 5/2003 | Smith | A61M 5/158 |
| | | | | 604/177 |
| 2008/0269695 | A1* | 10/2008 | Perouse | A61M 5/158 |
| | | | | 604/240 |

\* cited by examiner

*Primary Examiner* — Bhisma Mehta
*Assistant Examiner* — Larry R Wilson
(74) *Attorney, Agent, or Firm* — Hoglund & Pamias, PSC; Roberto J. Rios

(57) ABSTRACT

A safety needle device comprising a body piece including a rear end connected to a cannula and a front end having a needle for connecting to a patient, a sliding gap at the front end of the body piece, a lock button at a rear end of the body piece, a sliding piece adopting a locked position wherein the sliding piece is folded and locked onto the body piece and a sliding position wherein the sliding piece is unfolded and unlocked from the body piece; retaining flaps at a bottom of the sliding piece for receiving the fingers of a hand of a user when the needle device must be disconnected from the patient, and locking parts in the sliding piece to lock the sliding piece and the body piece in a position wherein the needle is removed from the patient and protected by walls of the sliding piece.

12 Claims, 2 Drawing Sheets

SAFETY NEEDLE DEVICE

BACKGROUND OF THE INVENTION

1. Field of the Invention

The present invention relates to a safety needle device, and more particularly refers to a safety needle retractable device employed in medical and hospital uses, such as blood extractions, drug injections, etc., and capable of permitting the safe extraction of a needle after use of the device.

2. Description of the Prior Art

Currently there are several types of procedures and devices for use when a doctor or nurse extract blood from a patient or have to inject a medicine, whether it is intramuscular or intravenous. In all cases a needle is necessary and, after the operation in the patient, the needle must be disposed without risks for the nurse and/or the doctor.

These types of procedures, in most cases, are manually made by the health worker, however in certain procedures, needle extraction systems are employed, which systems comprise tweezers shaped pieces that allow withdrawing the needle for disposal or integrated fin-like projections integrated in the needle cannula. While such systems partially meet the safety requirements in these procedures, in some cases, due to the primitiveness of such systems, they do not prevent the health workers from being exposed to accidents or inconveniences in the use of the available needle systems.

Several systems and devices are well known in the art, such as the following.

"Deltec's Gripper Plus" is a needle device that requires a single safe movement for operation. The fingers of a hand of the user are placed on each side of a base of the device and then, a finger of the other hand is placed on a safety arm of the device. The "Gripper Plus", as known in the art, has a cushioned platform for better patient comfort, a needle stabilizer and a protection in the injection area. It also has a removable outline to better handle needle removal. Information of this device available at the web site: PONER WEB SITE The "LifeGuard Safety Huber Needle", provided by Horizon Medical Products (HMP), is a device wherein the needle is trapped or retained after removal. Compared to other traditional devices, "LifeGuard's needle" is designed for a better control and safety with minor technique changes. Using the non-dominant hand, a safety hinge of the device must be taken between the index finger and the thumb, the hinge must then be pushed down against the skin of the patient where a needle receiving port is placed. Then the needle must be pulled along a needle-guide to a safety position. Information of this device is available at the web site: PONER WEB SITE "Surecan Safety Huber Needle" of B. Braun comprises a device with parts having different colors and it is available for needles numbers 19, 20 and 22. The "Surecan" does not contain any latex, to avoid allergic reactions, and it is DEHP free, thus it is compatible with chemical drugs and lipids. It allows for blood extraction and drug administration in one simple movement. The device has a base that is firmly stabilized with the non-dominant hand of the operator while the needle retracts by pulling from it, and the device has a safety clip that automatically sheathes the needle. Information of this device is available at the web site: PONER WEB BITE "LiftLoc Safety Infusion Set", manufactured by Specialized Health Products international Inc. and sold by Bard Access Systems, is a needle device with a robust cover which is capable of unfolding when the needle is extracted from a port of the device, thus effectively reducing the risk of accidental pricks. The device comprises a patient comfort pad (pillow) for patient comfort. It conveys an easy to use mechanism comprising wings that must be held and lifted. When the wings are lifted, the LiftLoc is automatically lifted from the port containing the needle in order to cover it. Information of this device is available at the web site: PONER WEB SITE "K-Shield" device, from Kawasami Laboratories America, Inc., is designed to protect professionals working in the oncology field from lesions during the removal of needles in subcutaneous ports. The device provides comfort for the patient, with no disturbances during the changing of the needle or when the same is placed in the patient. Information of this device is available at the web site: PONER NEB SITE "TriState-Centurion HuberGuard Safety Device", manufactured by Harmac and distributed by TriState Hospital Supply Corporation is a device that prevents occasional needle pricks when used jointly with the above mentioned "Centurion" device for removing and placing needles. The device has a small side faced needle that provides comfort for the patient and reduces bruising and port displacement. Information of this device is available at the web site: PONER WEB SITE In spite of the several devices available today in the market, the National Health Organization reports that two million workers in this sector worldwide experience percutaneous exposure or infectious diseases every year. Percutaneous lesions constitute the most common way of exposure to diseased blood, and the main cause in pathogen transmission to the blood.

While the above disclosed devices are well known and employed in the art with generally good performances, the inventor of the present invention is convinced that a better device may be developed to solve some inconveniences of the prior art, thus providing a better safety for extraction of needles for use by health care workers, mainly, keeping in mind that these workers are always exposed to accidents with sharp objects, specially pricks. A prick is one of the main causes in health related accidents when handling sharp devices, with the added risk of catching, by contagion, infectious diseases such as Hepatitis B Hepatitis C and HIV, pointing out that regrettably teaching doctors, interns, residents and nurses are the most affected workers.

SUMMARY OF THE INVENTION

Therefore, it is an object of the invention to provide a safety needle device capable of solving problems that are caused in the area of health related to accidents that occur when needles, suture needles, etc., need to be manipulated.

It is another object of the present invention to provide a safety needle device that fully reduces risks for health care workers when using needles in patients with contagious diseases.

It is another object of the present invention to provide a safety needle device, such as a bio-safety device for mainly reducing unnecessary injections, changing, among other actions, the use of intravenous needle in some procedures.

It is another object of the present invention to provide a safety needle device comprising a body piece including a rear end connected to a cannula and a front end having a needle for connecting to a patient; a sliding gap at the front end of the body piece; a lock button at a rear end of the body piece; a sliding piece defining a locked position wherein the sliding piece is folded and locked onto the body piece and a sliding position wherein the sliding piece is unfolded and unlocked from the body piece; retaining flaps at a bottom of the sliding piece for receiving some fingers of a user when the needle device must be disconnected from the patient, and locking means in the sliding piece to lock the sliding piece and the body piece in a position wherein the needle is removed from the patient and protected by walls of the sliding piece.

DESCRIPTION OF THE PREFERRED EMBODIMENT

Figures 1, 2:
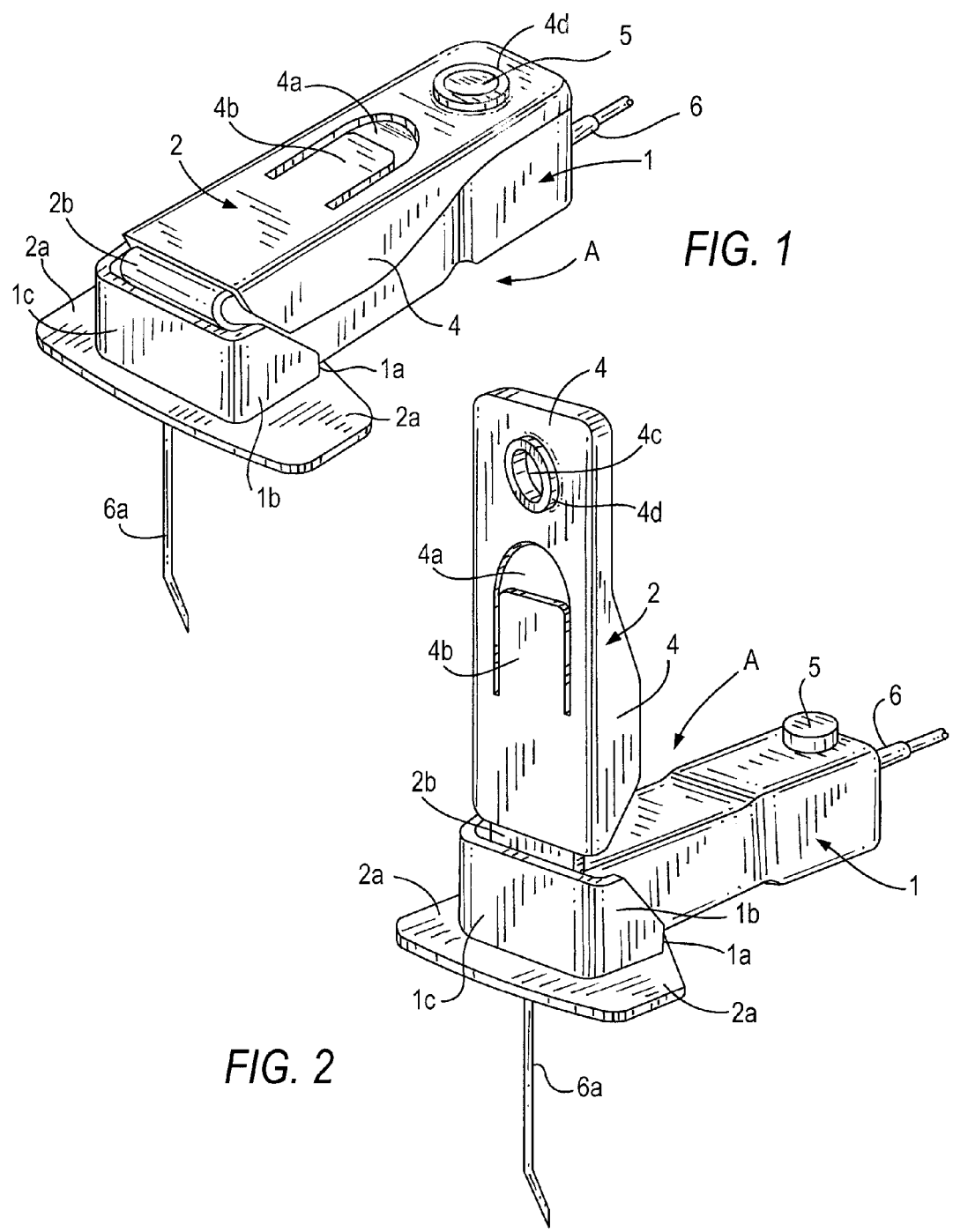
FIG. 1 shows a perspective view of the device according to a preferred embodiment of the invention, with the sliding piece folded and locked onto the body piece.
FIG. 2 shows a perspective view of the device, with the sliding piece unfolded.

According to the drawings the device of the present invention, generally indicated by reference "A", comprises a pair of pieces, namely a body piece 1 and a sliding piece 2, with piece 2 hinged on itself and mounted in the body piece 1. Sliding piece 2 may be made of only one piece and has a lower part 3 including side fixed flaps 2a capable of accommodating the fingers of a user and supporting a force onto the flaps when the needle is being removed, as will be explained below. Sliding piece 2 also has a hinge 2b defining an articulation between an upper part or head 4 that includes an inverse U-shaped slot 4a that, in turn, defines a tongue 4b. Head 4 also comprises a circular hole 4c on a rear or upper end that is opposite to hinge 2b, and is encircled by a circular ring 4d. At a bottom of lower part 3 a needle receiving hole 4e is defined.

Figures 3, 4:
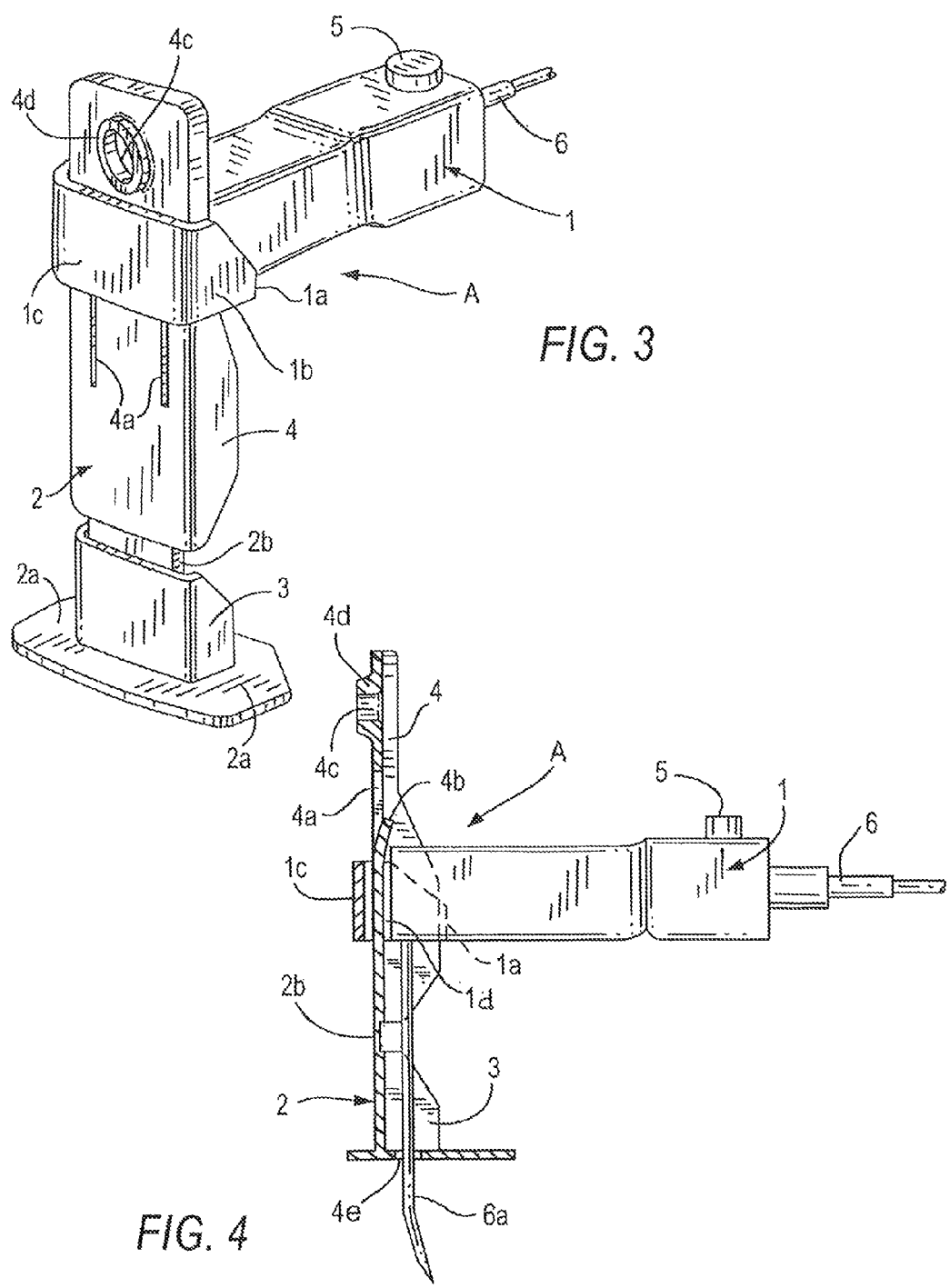
FIG. 3 shows a perspective view of the device, with the sliding piece partially slid down.
FIG. 4 shows a partial cross section view of the device, with the sliding piece partially slid down.

Body piece 1 may be a general quadrangular body having a rear end, at the right hand side of the drawings, and a front end, at the left hand side of the drawings, with a cannula 6 entering the rear end of body 1 and extending along the interior of the body to connect, in fluid communication, with a needle 6a appearing at the front end of the body. A receiving part defined by two perpendicular lateral projections 1a, FIG. 4, are connected to parallel lateral walls 1b, having an inclined configuration as shown, which walls 1b are joined by a frontal portion is that defines, with the front end of body 1, a gap 1d. A protuberance or button 5 is also provided at the rear end of body 1.

Sliding piece 2 is normally folded onto body 1, as shown in FIG. 1, with hole 4c being locked on button 5. Piece 2 can be unfolded and slid down when placed in a perpendicular way, as shown in FIGS. 2-4, with head 4 being capable of sliding through gap 1d. Tongue 4b is capable of sliding down through gap 1d but once the upper end of tongue 4b goes out of gap 1d the same can not be moved up because the end of the tongue will be retained by a bottom surface of body 1. This forms a lower lock of the sliding piece. In addition, circular ring 4d has a size larger than the one of the gap, therefore it does not permit the ring to pass through gap 1d, therefore forming an upper lock.

When the needle device must be disconnected from the patient, the proper way for the extraction of the injected needle is made by positioning the major and index fingers of the non-working hand of the user on flaps 2a. Sliding piece 2 is unlocked from button 5 and unfolded to take the position shown in FIGS. 2-4. When in this position, body piece 1 is moved up to remove the needle from the patient, making head 4 sliding down through gap 1d until the upper end of tongue 4b passes the lower end of gap 1d and moves out of the gap. In this condition, tongue 4b is locked against body 1 and prevented from moving up. In addition, circular ring 4d abuts against the upper surface of body 1 preventing sliding piece 2 from further sliding down. In this position, needle 6a is covered by lateral walls 4 and portion 3 of sliding piece 2. Under these conditions the needle can be removed without risks for the operator.

I claim:

1. A safety needle device comprising:
    a body piece including a rear end connected to a cannula, a lock button provided on said rear end, a front end having a needle for connecting to a patient, and a receiving part extending from said front end so that a sliding gap is formed between said receiving part and the front end of said body piece;
    a sliding piece having an upper part, a lower part connected to said upper part by a hinge and including retaining flaps configured to receive fingers of a user when the needle device must be disconnected from a patient, wherein said sliding piece is positioned inside said sliding gap between the receiving part and the front end of said body piece so that a locked positioned is defined when said sliding piece is folded and locked onto the lock button of said body piece and a sliding position is defined when the sliding piece is unfolded and unlocked from the lock button of said body piece; and
    a lower locking member protruding from said sliding piece towards said front end of the body piece and an upper locking member positioned above said lower locking member protruding from said sliding piece in a direction opposite to said lower locking member, wherein said lower locking member is configured to contact said body piece preventing downward movement of said body piece and said upper locking member is configured to contact said receiving part preventing upward movement of said body piece so that the sliding piece and the body piece are locked in a position where the needle is removed from the patient and protected by walls of the sliding piece.

2. The device of claim 1, wherein said lower part comprises a needle receiving hole.

3. The device of claim 1, wherein the lower locking member is a U-shaped slot defining a tongue with an upper end protruding from said sliding piece towards said front end of the body piece.

4. The device of claim 3, wherein the upper end of the tongue is configured to contact a bottom surface of said body piece preventing downward movement of said body piece.

5. The device of claim 3, wherein the upper end of the tongue is curved towards the front end of the body piece.

6. The device of claim 1, wherein the upper locking member is a circular hole encircled by a circular ring protruding from said sliding piece in a direction opposite to said lower locking member.

7. The device of claim 6, wherein the circular ring is configured to contact an upper surface of said receiving part preventing upward movement of said body piece.

8. The device of claim 6, wherein the circular ring has a dimension larger than the sliding gap, so that the circular ring is prevented from passing through the sliding gap.

9. The device of claim 6, wherein said sliding piece is locked onto said body piece when the lock button of said body piece is inserted into said circular hole.

10. The device of claim 6, wherein said sliding piece is unlocked from said body piece when the lock button of said body piece is removed from said circular hole.

11. The device of claim 1, wherein the sliding gap is defined by two perpendicular lateral projections extending from the sides of the body piece, said lateral projections being connected to parallel lateral walls that are joined by a frontal portion.

12. The device of claim 1, wherein the hinge comprises a narrowing portion in the sliding piece.

* * * * *